(12) United States Patent
Rajbhandary et al.

(10) Patent No.: US 11,826,125 B2
(45) Date of Patent: Nov. 28, 2023

(54) METHOD AND SYSTEM FOR BODY TEMPERATURE ESTIMATION USING A WEARABLE BIOSENSOR

(71) Applicant: Vital Connect, Inc., San Jose, CA (US)

(72) Inventors: Paurakh Lal Rajbhandary, San Jose, CA (US); Gabriel Nallathambi, San Jose, CA (US)

(73) Assignee: Vital Connect, Inc., San Jose, CA (US)

( * ) Notice: Subject to any disclaimer, the term of this patent is extended or adjusted under 35 U.S.C. 154(b) by 546 days.

(21) Appl. No.: 16/932,781

(22) Filed: Jul. 19, 2020

(65) Prior Publication Data

US 2022/0015643 A1  Jan. 20, 2022

(51) Int. Cl.
*A61B 5/01* (2006.01)
*A61B 5/0205* (2006.01)
*A61B 5/00* (2006.01)
*A61B 5/11* (2006.01)
*G16H 50/30* (2018.01)
*G16H 40/67* (2018.01)
*G16H 50/20* (2018.01)
(Continued)

(52) U.S. Cl.
CPC ............ *A61B 5/01* (2013.01); *A61B 5/02055* (2013.01); *A61B 5/1118* (2013.01); *A61B 5/726* (2013.01); *A61B 5/7257* (2013.01); *A61B 5/7267* (2013.01); *G01K 1/14* (2013.01); *G01K 13/20* (2021.01); *G16H 40/67* (2018.01); *G16H 50/20* (2018.01); *G16H 50/30* (2018.01); *G16H 50/70* (2018.01); *A61B 5/02438* (2013.01); *A61B 5/0816* (2013.01); *A61B 2560/0252* (2013.01); *A61B 2562/0219* (2013.01)

(58) Field of Classification Search
CPC . A61B 2560/0252; A61B 5/01; A61B 5/7264; A61B 5/7257; A61B 5/726; A61B 5/7267; A61B 5/7275; A61B 5/725; A61B 5/0008; A61B 5/02055; G01K 3/00; G01K 13/20
See application file for complete search history.

(56) References Cited

U.S. PATENT DOCUMENTS

| | | | | |
|---|---|---|---|---|
| 5,050,612 A | * | 9/1991 | Matsumura | A61B 5/14532 374/E13.002 |
| 2005/0043631 A1 | * | 2/2005 | Fraden | G01K 13/20 374/E7.042 |

(Continued)

OTHER PUBLICATIONS

Morette, N. (2018). What is the difference between wavelet transform and STFT?—quora. Quora. Retrieved Dec. 1, 2022, from https://www.quora.com/What-is-the-difference-between-wavelet-transform-and-STFT (Year: 2018).*

(Continued)

*Primary Examiner* — Eric F Winakur
*Assistant Examiner* — Elina Sohyun Ahn
(74) *Attorney, Agent, or Firm* — Shih IP Law Group, PLLC

(57) ABSTRACT

The present application relates to a device, system, and method for determining patient body temperature based on a multi-modal wearable biosensor applied to the surface of the body that measures multiple physiological, physical, and skin-surface/microclimatic thermal parameters, derives additional instantaneous parameters, learns contextual parameters based on temporal dynamics, and employs ensemble model fusion method to estimate core body temperature.

20 Claims, 5 Drawing Sheets

(51) Int. Cl.
*G16H 50/70* (2018.01)
*G01K 1/14* (2021.01)
*G01K 13/20* (2021.01)
*A61B 5/08* (2006.01)
*A61B 5/024* (2006.01)

(56) References Cited

U.S. PATENT DOCUMENTS

| | | | |
|---|---|---|---|
| 2005/0245839 A1* | 11/2005 | Stivoric | A61B 10/0012 |
| | | | 374/E1.004 |
| 2012/0123232 A1 | 5/2012 | Najarian | |
| 2017/0071487 A1 | 3/2017 | Ritscher | |
| 2017/0220752 A1 | 8/2017 | Murphy | |
| 2017/0238811 A1* | 8/2017 | Buller | A61B 5/7278 |
| 2018/0108440 A1 | 4/2018 | Stevens | |
| 2018/0242850 A1* | 8/2018 | Ellis | A61B 5/02007 |
| 2019/0110755 A1* | 4/2019 | Capodilupo | G06K 9/6282 |
| 2019/0350462 A1 | 11/2019 | Biederman | |
| 2020/0323435 A1* | 10/2020 | Selvaraj | A61B 5/01 |
| 2021/0322098 A1* | 10/2021 | Bourquin | A61B 5/0531 |

OTHER PUBLICATIONS

Costa, M., & Monteiro, M. (2016). Bias-correction of Kalman filter estimators associated to a linear state space model with estimated parameters. Journal of Statistical Planning and Inference, 176, 22-32. https://doi.org/10.1016/j.jspi.2016.04.002 (Year: 2016).*
International Search Report and Written Opinion from International Application No. PCT/US2021/041238 dated Oct. 27, 2021, 11 pages.

* cited by examiner

Algorithm 1: Ensemble Model & Its Fusion with Meta-model For Body Temperature Determination

```
/* ********************************************************** */
/* Training                                                   */
/*                                                            */
```
1 function trainModelsAndMetaModels ($t_{ref}$, $F_{ref}$):
   Input  : Reference temperature: $t_{ref}$,
              Input features: $F_{ref}$
   Output: Model & meta-model parameters $param$
2 Determine model parameters for all models with all possible subset combination of feature set $F_i \subset F_{ref}$ and store in $param$ Determine meta-model parameters for all models and store in $param$
```
/* ********************************************************** */
/* Deployment                                                 */
/*                                                            */
```
3 function determineBodyTemperature ($F, param$):
   Input  : Feature bank: $F$,
              Ensemble model parameters: $param$
   Output: Body temperature $\bar{t}_b$
   // Obtain model and meta-model outputs for ensemble of $N$ models
4 for $i \leftarrow 1$ to $N$ do
      // Obtain estimate from ensemble of $i$-th model of $N$ models
5     repeat
6        Estimate intermediate value with $i$-th estimator($E_i$) using feature set $F_M^{E_i}$
7        if *intermediate value is not valid because all features are not available* then
8           Drop unavailable feature $F_{invalid}$ from the feature set $F_M^{E_i}$ s.t. $F_M^{E_i} = F_M^{E_i} \setminus F_{invalid}$;
9        else
10          Apply non-linear mapping function $\sigma()$ followed by affine mapping function to the intermediate estimate using learned parameters & store as $\hat{t}_b^{model-i}$
11          Register used feature set for the $i$-th model $F_M^{E_i}$
12        end
13    until *valid estimate for $i$-th model is not obtained*;
      // Obtain weights for fusion of $N$ models
14    Extract meta-features from registered feature set $F_M^{E_i}$
15    Estimate error based on meta features
16    Convert error into an inversely correlated weight $w_i$
17 end
   // Model Fusion
18 Normalize weights s.t. $w_i = \frac{w_i}{\sum_{j=1}^{N}(w_j)}$
19 $\bar{t}_b = \sum_{i=1}^{N} w_i \hat{t}_b^{model-i}$

FIG. 3

METHOD AND SYSTEM FOR BODY TEMPERATURE ESTIMATION USING A WEARABLE BIOSENSOR

BACKGROUND

Core temperature is the temperature measured at the deep tissues of the body such as abdominal, thoracic and cranial cavities, and is indicative of the person's health and physiological state. The hypothalamus is the controlling center for body temperature regulation, and is fed by cold and heat sensing thermoreceptors in the skin (cutaneous receptors), cornea, urinary bladder, liver and hypothalamus. Hypothalamus regulates temperature via. mechanisms such as conduction, convection and radiation mechanisms to maintain temperature within a narrow margin with slight diurnal variation usually of peak-to-peak amplitude of ~1 C due to circadian rhythm with temperature rising during the day time and dropping during the night and sleep time.

The body temperature is correlated and affected by physiological and ambient parameters and is maintained by the interaction of heat production, conservation and dissipation from the body. Heat is generated in the body by the steady process of chemical oxidative metabolism and the intermittent process of muscular activities. The rate of loss of the produced heat occurs by physiological processes including vasoconstriction and diversion of blood flow away from the skin surface (skin vasoconstriction, piloerection, decrease sweating, increased muscle contraction, non-shivering thermogenesis, seeking warm clothing or environments). The dissipation of heat may occur by the physical mechanism of convection, radiation and evaporation, and a tradeoff between them exists in different setting. For example, convection is more efficient during high ambient wind setting, evaporation is the dominant heat dissipation mechanism during high temperature ambience but less efficient in high humidity. Breathing and ingestion of food or drink can also cause slight change in body temperature but is a minor mechanism of heat changes.

Change in body temperature outside of normal range may occur either due to inability of the body to attain the set point temperature or the change in the setpoint itself. The ambient and physiological parameters of the body may indicate deviation of body temperature from the normal range. The former can be caused due to exposure to extreme environment or stress such as high or low temperature or high humidity with little ventilation. For example, the hypothalamic set point or target temperature is not altered in persons suffering from hyperthermia due to exercise and strenuous physical work that can raise core temperature outside the normal range. Another example could be an open water swimmer exposed to low temperature may undergo hypothermia, which results in hypometabolism causing diminished body activity overall. The latter effect of change of hypothalamic set point causes fever or pyrexia.

The gold standard for measuring core temperature is pulmonary arterial or esophageal catheter but these require invasive probe placement, which is quite impractical, and rarely used outside the critical care ward. Other more prevalent clinical practice of assessing body temperature includes using urinary catheter, rectal probe, oral thermometer and axillary thermometer. There is a tradeoff between invasiveness, accuracy, precision, requirement of human intervention/input, frequency and continuous availability of body temperature profile, and while pulmonary arterial or esophageal catheter and even urinary bladder or rectal catheters can provide a more accurate core body temperature indication in a continuous setting, it is invasive and usually restricts patients to within bedside. The present application addresses the need of providing the best solution in this tradeoff for optimally improving the clinical outcome by providing accurate and continuous body temperature using non-invasive sensors.

In this application, measurements of various physiological, physical, and skin-surface/microclimatic thermal entities from one or more sensors encapsulated in one or more devices is applied to estimate core body temperature using a novel ensemble method of learning baseline model and meta-model based on different physiological and environmental parameters.

SUMMARY

In one example embodiment, a method to determine patient body temperature using a wearable sensor, including: measuring at least one of ambient, instantaneous, or patient condition sensor data; extracting from the at least one of ambient, instantaneous, or patient condition sensor data, two classes of parameters including: contextual parameters that may be learned based on at least one of: prior data, temporal dynamics of physiological, physical, and skin-surf ace/microclimatic thermal parameters, and instantaneous parameters that may be entities that may be derived based on the sensor data; processing the contextual parameters and instantaneous parameters by utilizing a plurality of trained models by a plurality of estimators to determine a plurality of body temperature estimates, respectively; implementing bias and trend correction procedures to correct the plurality of body temperature estimates by improving trend matching and accuracy of the plurality of body temperature estimates; determining a confidence level of each of the plurality of body temperature estimates based on meta-features of a feature set that each of the plurality of estimators uses; and determining a final body temperature based on a combination of the plurality of body temperature estimates weighted based on the confidence level of each of the body temperature estimates.

In another example embodiment, a non-transitory computer-readable medium, associated with a wearable sensor to determine patient body temperature, storing instructions that, when executed, cause one or more processors to perform operations including: measuring at least one of ambient, instantaneous, or patient condition sensor data; extracting from the at least one of ambient, instantaneous, or patient condition sensor data, two classes of parameters including: instantaneous parameters that may be entities that may be derived based on the sensor data, and contextual parameters that may be time series of the instantaneous parameters; processing the contextual parameters and instantaneous parameters by utilizing a plurality of trained models by a plurality of estimators to determine a plurality of body temperature estimates, respectively; implementing bias and trend correction procedures to correct the plurality of body temperature estimates by improving trend matching and accuracy of the plurality of body temperature estimates; determining a confidence level of each of the plurality of body temperature estimates based on meta-features of a feature set that each of the plurality of estimators uses; and determining a final body temperature based on a combination of the plurality of body temperature estimates weighted based on the confidence level of each of the body temperature estimates.

In yet another example embodiment, a wearable sensor including a memory storing instructions to determine patient body temperature, and that, when executed, cause one or more processors to perform operations including: measuring at least one of ambient, instantaneous, or patient condition sensor data; extracting from the at least one of ambient, instantaneous, or patient condition sensor data, two classes of parameters including: instantaneous parameters that may be entities that may be derived based on the sensor data, and contextual parameters that may be time series of the instantaneous parameters determined by smoothing or filtering with different kernels including at least one of: low pass filtering, band pass filtering, high pass filtering, or wavelets to determine short-term dynamics of the instantaneous parameters, and wherein as increased sensor data is accumulated, the smoothing may be performed over longer time frames than the smoothing for the short-term dynamics to determine long-term dynamics of the instantaneous parameters; processing the contextual parameters and instantaneous parameters by utilizing a plurality of trained models by a plurality of estimators to determine a plurality of body temperature estimates, respectively; implementing bias and trend correction procedures to correct the plurality of body temperature estimates by improving trend matching and accuracy of the plurality of body temperature estimates; determining a confidence level of each of the plurality of body temperature estimates based on meta-features of a feature set that each of the plurality of estimators uses; and determining a final body temperature based on a combination of the plurality of body temperature estimates weighted based on the confidence level of each of the body temperature estimates.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the brief description that follows, examples and embodiments are described as illustrations only since various changes and modifications will become apparent to those skilled in the art from the following detailed description. The use of the same reference numbers in different figures indicates similar or identical items.

FIG. 3 shows an example algorithm for implementing one or more embodiments for body temperature estimation using a wearable biosensor;

DETAILED DESCRIPTION

Figure 1:
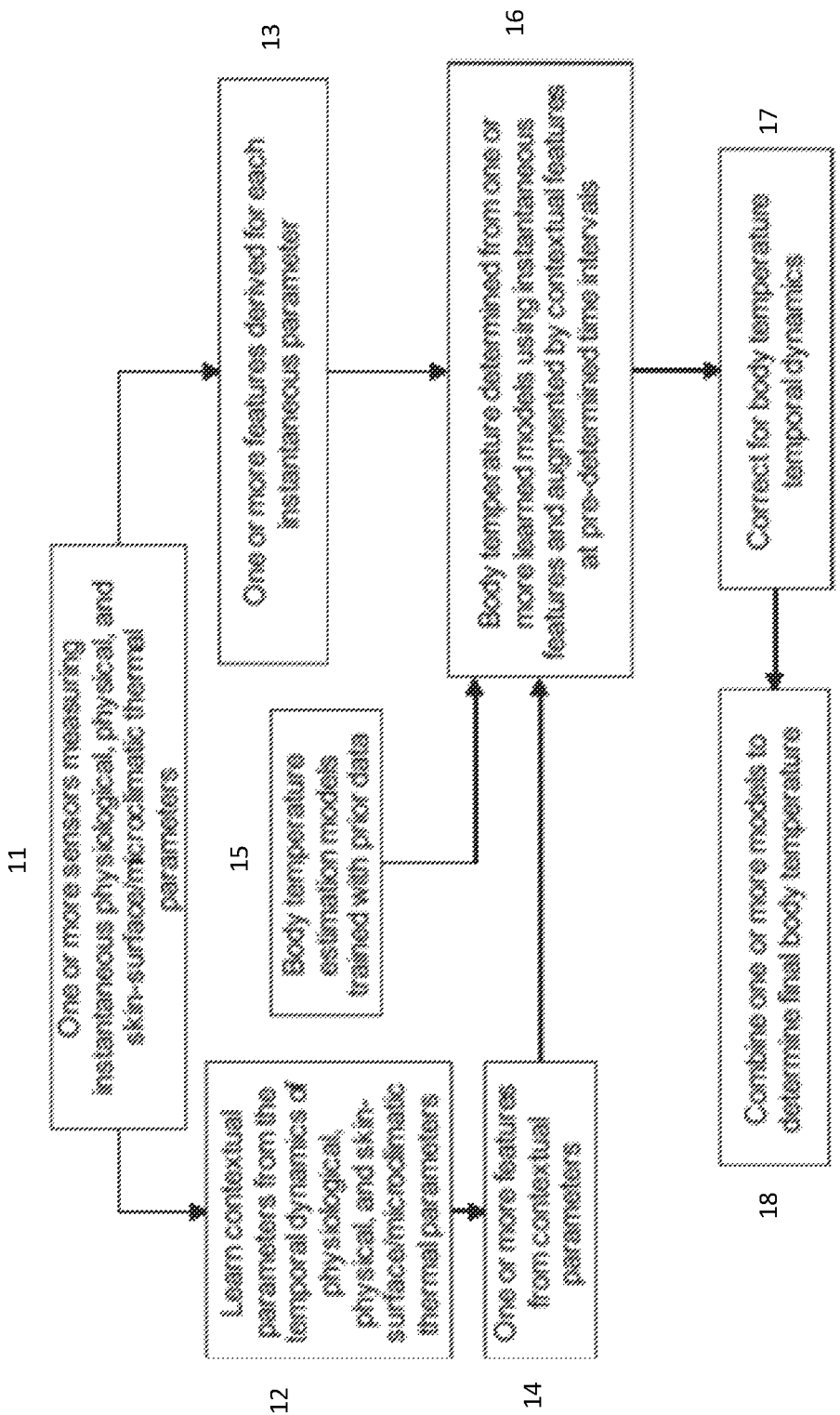
FIG. 1 shows an example block diagram for implementing one or more embodiments for body temperature estimation using a wearable biosensor.

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current example embodiment. Still, the example embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and illustrated in the drawings, may be arranged, substituted, combined, separated, and designed in a wide variety of different configurations, all of which are explicitly contemplated herein.

FIG. 1 shows an example block diagram for implementing one or more embodiments of the system and method for determining patient body temperature (denoted as BodyTemp here forth) using a wearable biosensor. The body temperature determination/estimation using a wearable biosensor includes an ensemble of mathematical and machine learning models of a human body's complex homeostatic thermoregulation mechanism and an adaptive fusion method that combines these models for optimal continuous estimation of the core body temperature.

Accordingly, in FIG. 1 at 11 one or more wearable sensors may be used to measure ambient, instantaneous, and/or patient conditions which may include physiological, physical, skin-surface/microclimatic thermal parameters, temperature, humidity, vitals, and activity metrics. Based on the sensor stream, there may be two classes of parameters that may be extracted including contextual parameters that may be learned based on prior data, and/or temporal dynamics of physiological, physical, and skin-surface/microclimatic thermal parameters of the sensor streams at 12, and instantaneous parameters that may be entities that may be extracted or derived based on the current measurement of the sensor at 13. Contextual features may range from smoothing with different kernels or may utilize domain knowledge to obtain derived features which may include an estimate of change of heart rate from the basal heart or respiratory rate, physiological metrics normalized by accelerometer-based activity metrics, personalized parameters that learns about the patient's baseline physiological state and more at 14. These derived features or its subset may be used by an ensemble of trained models for a set of BodyTemp estimates at 15. Further, these features may be used by an ensemble of estimators including but not limited to machine learning models, recursive filters, mathematical forward models, etc., each computing the body temperature estimate at 16. These estimators may be trained using prior collected data containing these parameters and also ground reference body temperature estimate. Necessary bias and trend correction steps may be included to improve the trend matching and accuracy of the algorithm at 17. The confidence of each of these estimates may be determined based on meta-features of a feature set that each of these estimators uses. The final body temperature may be based on combining the estimates weighted based on the confidence of the estimation at 18.

Figure 2:
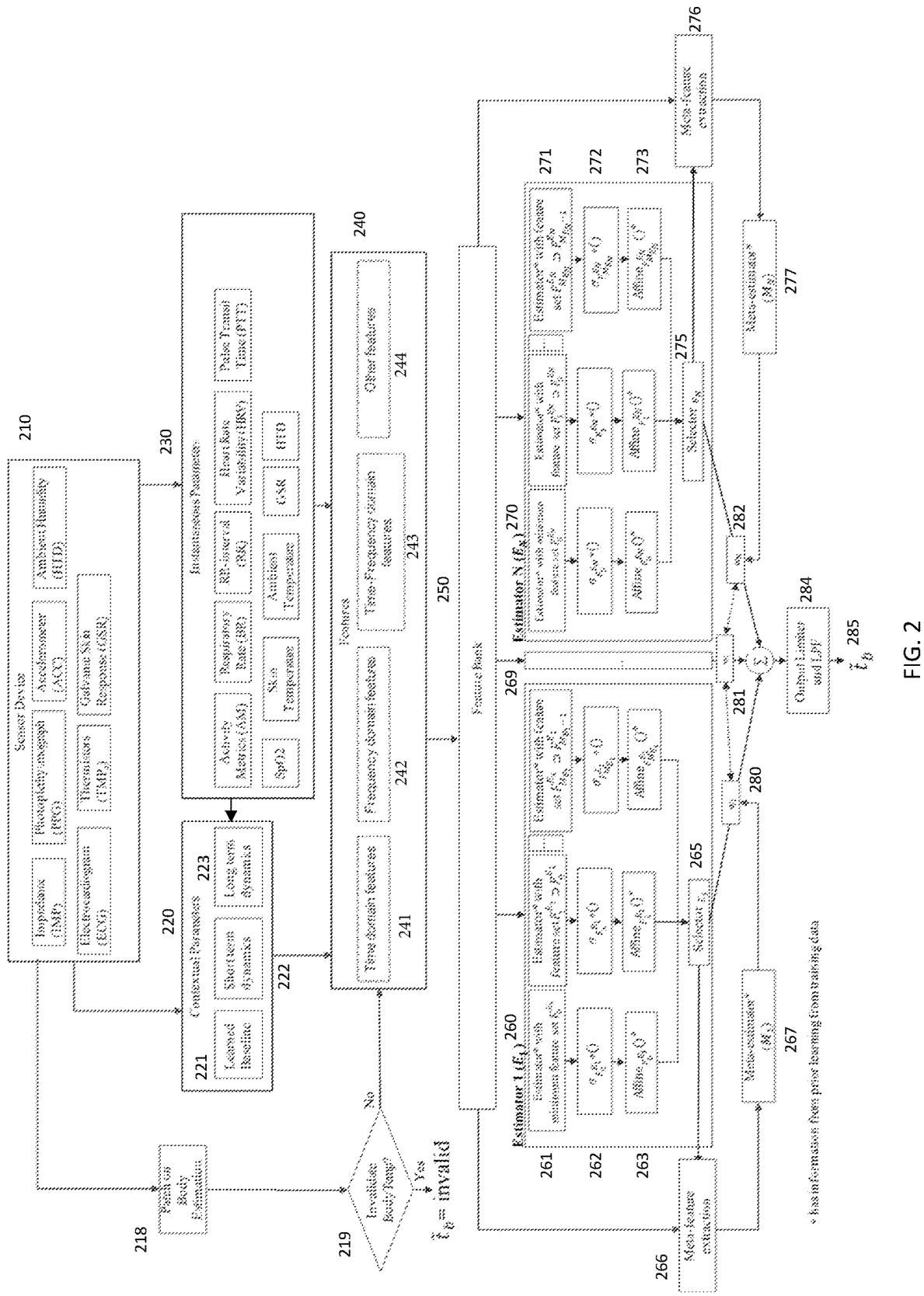
FIG. 2 shows an example block diagram for implementing core body temperature estimation algorithm.

FIG. 2 shows additional details of the FIG. 1 system and method for patient body temperature measurement. A wearable sensor device 210 may include multiple sensors including one or more temperature transducers for measurement of skin and microclimatic temperatures, Thermistors (TMP), accelerometer (ACC), photoplesthysmograph (PPG) sensor, electrocardiograph (ECG) sensor, impedance (IMP) sensor, ambient humidity (HTD) sensor, galvanic skin response (GSR) sensor, and other relevant sensors. The sensors may be enclosed in one or more wearable devices such as adhesive patch sensor, pendant, wrist-band, wrist-watch or an electronic module adhered to the body are within the scope of this invention.

The multi-sensor measurements may be categorized broadly into two mutually non-exclusive sets. First set includes status measurements that allow detection of whether the patch is adhered and in thermal equilibrium to the body and includes measurements such as body impedance and ECG signal. The second set includes multiple physiological, physical, and skin-surface/microclimatic thermal parameters, in addition to other derived information to determine the core body temperature.

The patient body temperature assessment starts with detection of patch on-body status based on a function derived from input signal measurements at 218. For example, the function to estimate the patch on-body status at 218 may be a logical combination (logical AND/logical OR) of impedance measurements fed to a differentiator and compared against a threshold i-th and zero QRS complexes detected in ECG signal in a 20-second non-overlapping window. If patch is detected as removed from the body, then the body temperature may be invalidated at 219. Then, the entire aforementioned process may be reset and repeated till patch is detected as adhered to the body.

Once the estimation of the body temperature is active, the aforementioned sensors 210 is utilized to estimate at least one or more physiological, physical, and skin-surface/microclimatic thermal parameters including but not limited to: activity metrics (AM) intensity, respiratory rate (BR), heart rate variability (HRV), heart rate (not shown), relative heart rate (not shown), pulse transit time (PTT), SpO2, skin temperature, galvanic skin response (GSR), and ambient humidity (HTD) at 230. Further, information from the sensors may be utilized to estimate two sets of parameters: Contextual Parameters 220 and Instantaneous Parameters 230. Instantaneous Parameters 230 may be based on the current measurement of information by the sensors, whereas Contextual Parameters 220 may be information that is learnt about the patient based on temporal data.

The following metrics or more relevant features may be used for instantaneous parameters 230: Accelerometer derived parameters such as breathing rate based on chest wall movements, and intensity of activity, i.e. Activity Metrics (AM) as a function of area under the curve of each of the accelerometer axis. ECG sensor derived parameters such as RR-interval (RR) computed by detecting QRS complexes of ECG, heart rate variability (HRV), and ECG derived breathing rate including Respiratory Rate (BR). Optical sensor derived parameters such as SpO2 based on at least two wavelength PPG optical sensor transmittance or reflectance data, and pulse transit time (PTT) based on the difference of corresponding features in the ECG and PPG signal. The skin and microclimatic temperatures may be based on direct insulated temperature sensor data. Other relevant physiological and ambient sensor and inputs such as galvanic skin response (GSR), and ambient humidity (HTD) may also be used as instantaneous parameters 230.

The following metrics or other relevant entities may be used as contextual parameters 220. Contextual parameters 220 entails learning and estimating the underlying physiological parameters of the patient such as resting heart rate, respiratory rate, or other baseline features of the patients. For example, by computing the difference between instantaneous heart rate and learned resting heart rate, the personalized relative heart rate or learned baseline 221 may be obtained. In an example embodiment, contextual parameters 220 include time series of instantaneous parameters 230 that may be smoothened or filtered with different kernels including low, band, or high pass filtering, and wavelets, etc., to determine the short-term dynamics 222 of the instantaneous parameters. As more data is accumulated, contextual parameters 220 further include the long-term dynamics 223 of the instantaneous parameters that can be determined through smoothening over longer time frames. The long-term dynamics 223 thereby increases the accuracy and precision of the contextual parameters 220 that may be then used to compute features for the body temperature estimation. Therefore, filtering instantaneous parameters may obtain short and/or long-term dynamics, which are a type of contextual parameters.

The aforementioned instantaneous parameters 230 and contextual parameters 220 may then be processed through features extraction schemes 240. In one example, the instantaneous parameters 230 and contextual parameters 220 may be processed in overlapping or non-overlapping time windows to compute the varying degree of moments such as mean, standard deviation, skew, kurtosis, etc., and measure dispersion such as mean absolute difference, median absolute deviation, coefficient of variation, entropy, etc., to derive the time-based or time domain features 241. In another example, the instantaneous parameters 230 and contextual parameters 220 may be processed in time windows to compute the statistics (for example, maximum, minimum, average, entropy, kurtosis, etc.) of power density in different frequency sub-bands, cross spectrum, and coherence to derive the frequency-based or frequency domain features 242. In another example, the instantaneous parameters 230 and contextual parameters 220 may be processed in time windows to compute the statistical information from short-term Fourier transform and wavelet transform to derive time-frequency domain features 243. Further, one of ordinary skill in the art would appreciate that the instantaneous parameters 230 and contextual parameters 220 may be processed to derive other features 244. The derived information may be appended into a universal set feature bank 250 for further processing.

FIG. 3 shows an example algorithm for an ensemble model and its fusion with meta-model techniques for body temperature determination. An array of estimators 260, 269, 270 that estimate the core body temperature based on the subset of the feature bank 250 and prior training data that contains these features and reference body temperature. Estimators 261, 271 may include methods that involve machine learning models including regression, support vector machines, neural network, genetic estimation algorithm, non-parametric or parametric methods, recursive filters, Kalman filters, etc. A non-linear transformation 262, 272 such as a sigmoid function may be used to post-process the output of these models that maximizes the similarity of the trend of the signal measured by metrics such as Pearson's correlation coefficient. Following this, a linear transformation 263, 273 may be utilized to minimize the overall differences between the signal using metrics such as Root Mean Square Error (RMSE) of the core temperature to the reference temperature. The order of non-linear to linear transformation may be utilized to firstly optimize the time series trend or the shape of the core temperature profile and then perform the linear transformation which does not affect the correlation coefficient. Within each estimator 260, 270 multiple versions may be trained based on availability of feature set and a selector 265, 275 may be employed to pick the high performing estimator. Using a selector 265, 275 that selects an estimate from multiple sub-versions based on availability of feature set allows the algorithm to run adaptively when some features may not be valid for providing higher temperature estimate availability.

Further, in FIG. 2 an array of N core body temperature may be obtained from each estimator class $E_i$ 260, 270. For each of the i-th estimator, there may be multiple sub-models 261, 271 that may be attempted with features sets ranging from most information available feature set $$F_{M_{E_i}}^{E_i}$$

to minimum information available feature set $F_O^{E_i}$. The selector 265, 275 picks the estimator that provides a valid estimate with a highest feature available for that estimator class. This ensures that for each estimator 261, 271, estimation may be performed with designated full set of features when available, and the estimator class can fall back to back-up estimator if some elements or features from the feature set is not available, and this methodology provides a good compromise between availability and accuracy of the estimation. At 262, 272 the estimate may be passed through a non-linear transformation function $$\sigma_{F_j^{E_i}}$$

for i-th estimator and j-th sub-model that may be trained to maximize the trend or correlation in the estimate to the reference. This may then be followed at 263, 273 by affine transformation that allows minimization of error which could be captured in metrics such as mean square error. This affine transformation may be supported with calibration temperature which may control the zero-frequency component of the estimate to increase the accuracy of the estimate.

For each of the estimator models 260, 269, 270 and sub-models 261, 271, corresponding meta-models implemented by Meta-estimators 267, 277 may be trained with training data using meta-features 266, 276 to predict the emphasis or confidence score each of the models may be given when combining the models. Meta-features 266, 276 of the estimates may be windowed statistics such as measure of dispersion, varying degree of moments, correlations between features, etc., and these may indicate the quality of the features that may be used for the estimation and hence provides the magnitude of confidence to be assigned to each estimator. The magnitude of measure of confidence in accuracy and precision of the estimate may be used as weights $w_i$ 280, 281, 282 for each of i-th estimator to fuse N core body temperature estimate into a single estimate at 283. This may be followed by additional filtering and output limiter at 284 that sets the time-constant to possible change in temperature trend corresponding to actual physiological changes and may be outputted as the estimated core body temperature at 285.

Figure 4:
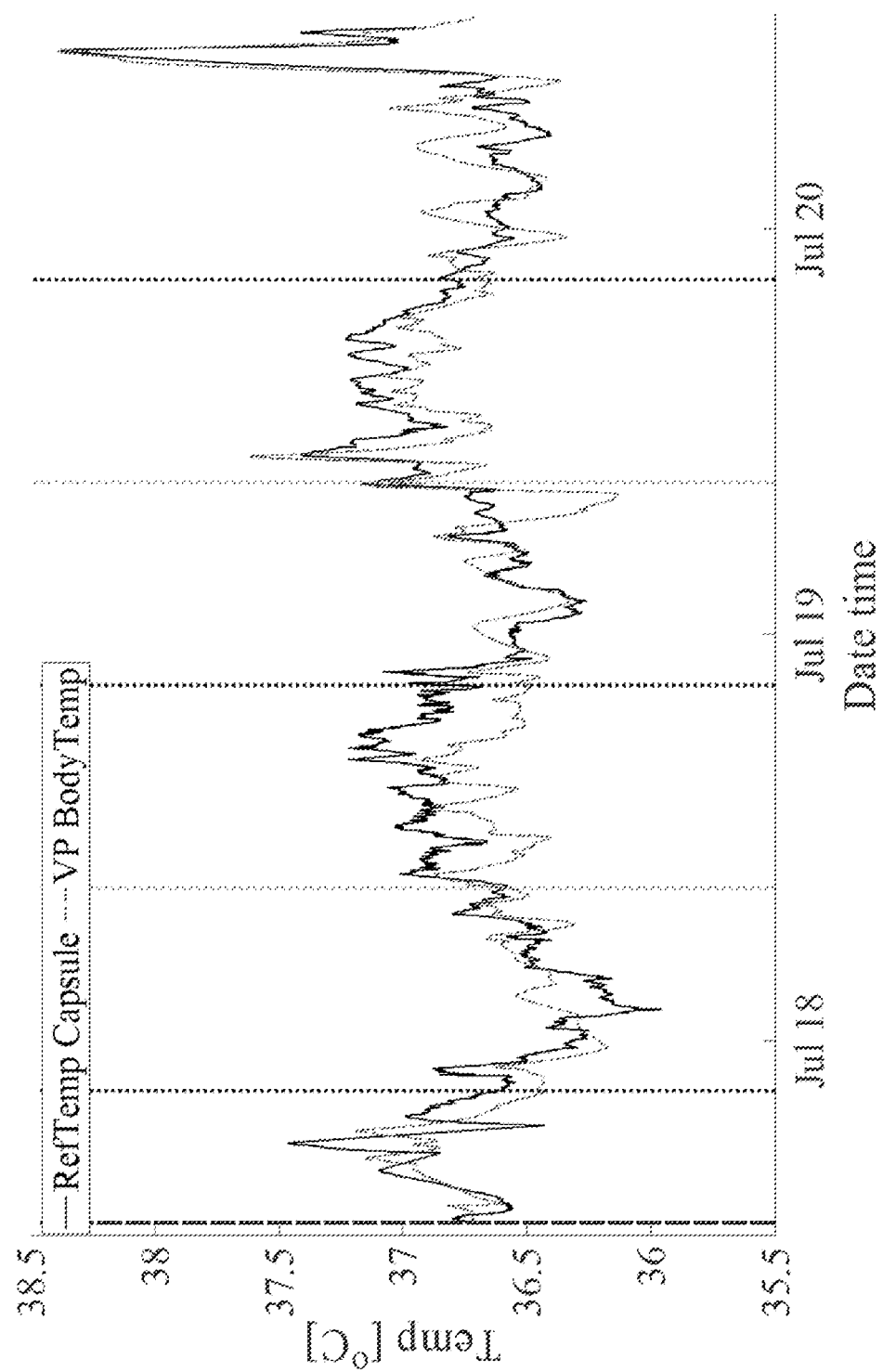
FIG. 4 shows an example illustration of a sample BodyTemp estimate compared with reference body temperature obtained from an ingestible temperature pill.

FIG. 4 shows validation of the BodyTemp estimate as implemented by the above methods compared with reference body temperature obtained from an ingestible temperature pill. The reference body temperature pill clearly shows the circadian rhythm pattern with temperature varying periodically throughout the day. The body temperature determined by the body temperature determination/estimation method as described above also shows similar trend and may be closely tracking the reference temperature.

Figure 5:
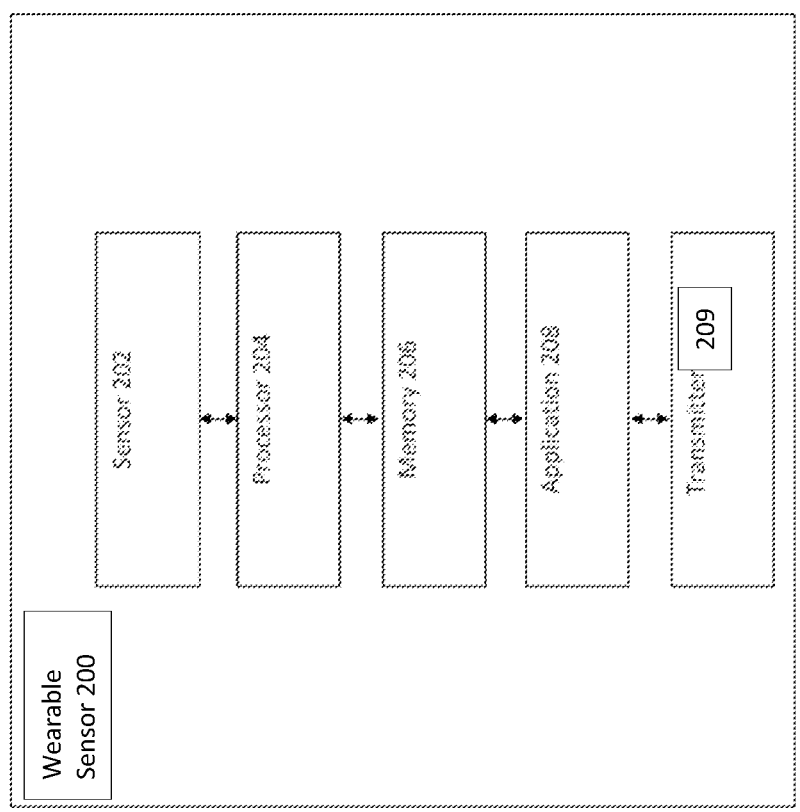
FIG. 5 shows an example illustration of a wearable sensor device in accordance with an embodiment for body temperature estimation using a wearable biosensor.

FIG. 5 illustrates a wearable sensor device 200 further describing sensor device 210 in accordance with an example embodiment. The wearable sensor device 200 includes a sensor 202, a processor 204 coupled to the sensor 202, a memory 206 coupled to the processor 204, an application 208 coupled to the memory 206, and a transmitter 209 coupled to the application 208. The wearable sensor device 200 may be attached, in any orientation, to a user. The sensor 202 obtains data from the user and transmits the data to the memory 206 and in turn to the application 208. The processor 204 executes the application 208 to determine information regarding instantaneous and contextual parameters that may be extracted to model the interactions between the human body and the environment to determine the core body temperature. The information may be transmitted to the transmitter 209 and in turn relayed to another user or device.

One of ordinary skill in the art readily recognizes that the wireless and wearable sensor device 200 may utilize a variety of devices for the sensor 202 including but not limited to uni-axial accelerometer, bi-axial accelerometer, tri-axial accelerometer, gyroscope, electrodes, pressure sensor, photoplethysmograph (pulse oximeter sensor), IMP sensor, PPG sensor, ACC sensor, HTD sensor, ECG sensor, TMP sensor, and GSR sensor that would be within the spirit and scope of the present application. One of ordinary skill in the art readily recognizes that the wearable sensor device 200 may utilize a variety of devices for the processor 204 including but not limited to microprocessors, controllers, and microcontrollers and that would be within the spirit and scope of the present invention. In addition, one of ordinary skill in the art readily recognizes that a variety of devices may be utilized for the memory 206, the application 208, and the transmitter 209 and that would be within the spirit and scope of the present application.

The present application utilizes a multi-sensor device from which instantaneous and contextual parameters may be extracted to model the interactions between the human body and the environment to determine the core body temperature. As the patient continues to wear the patch, more data allows contextual parameters to capture the baseline state of the patient, and add more features for increasingly more accurate estimate of the core body temperature. This approach also makes the method to be personalized to individual patient with more individual data. A plurality of estimator algorithms may be applied that provides estimates with different level of availability of inputs and a meta-model based fusion algorithm provides an adaptive method of combining the ensemble model into a single estimate that is more robust and accurate. The body temperature determination/estimation method provides a more stable and accurate body temperature estimate compared to single sensor measurements that can be easily contaminated and affected by external environment.

With regard to the components, results, diagrams, outputs, graphs, and operations depicted in and described in accordance with FIGS. 1-5, any of the operations and sub-operations of extracting instantaneous and contextual parameters to model the interactions between the human body and the environment to determine the core body temperature may be implemented as non-transitory computer-readable instructions stored on a computer-readable medium. The computer-readable instructions may, for example, be executed by the one or more processors of a wireless and wearable sensor, as referenced herein, having a network element and/or any other device corresponding thereto, particularly as applicable to the applications and/or programs described above.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method to determine patient body temperature using a wearable sensor, comprising:
   measuring at least one of ambient, instantaneous, or patient condition sensor data of a patient;
   extracting from the at least one of ambient, instantaneous, or patient condition sensor data of the patient, instantaneous parameters that are entities that are derived based on the sensor data of the patient;
   processing contextual parameters and the instantaneous parameters by utilizing a plurality of trained models by a plurality of estimators to determine a plurality of body temperature estimates, respectively, wherein the contextual parameters are learned based on at least one of: personalized prior physiological data of the patient and temporal dynamics of physiological, physical, and skin-surface/microclimatic thermal parameters of the patient;
   implementing bias and trend correction procedures to correct the plurality of body temperature estimates by improving trend matching and accuracy of the plurality of body temperature estimates;
   determining a confidence level of each of the plurality of body temperature estimates based on meta-features of a feature set that each of the plurality of estimators uses; and
   determining a final body temperature based on a combination of the plurality of body temperature estimates weighted based on the confidence level of each of the body temperature estimates.

2. The method of claim 1, wherein the ambient, instantaneous, or patient condition sensor data includes physiological, physical, skin-surface/microclimatic thermal parameters, temperature, humidity, vitals, and activity metrics.

3. The method of claim 1, wherein the contextual features parameters include at least one of: learned baseline, short-term dynamics, and long-term dynamics.

4. The method of claim 3, further comprising smoothing the contextual parameters with different kernels.

5. The method of claim 1, further comprising utilizing domain knowledge of the contextual parameters to obtain derived features.

6. The method of claim 5, wherein the domain knowledge to obtain derived features include at least one of: an estimate of change of heart rate from the basal heart or respiratory rate, physiological metrics normalized by accelerometer-based activity metrics, or personalized parameters reflective of a patient's learned baseline physiological state.

7. The method of claim 1, wherein the plurality of trained models utilized by the plurality of estimators include machine learning models, recursive filters, and mathematical forward models.

8. A non-transitory computer-readable medium, associated with a wearable sensor to determine patient body temperature, storing instructions that, when executed, cause one or more processors to perform operations comprising:
   measuring at least one of ambient, instantaneous, or patient condition sensor data of a patient; extracting from the at least one of ambient, instantaneous, or patient condition sensor data of the patient, two classes of parameters including:
   instantaneous parameters that are entities that are derived based on the sensor data of the patient, and
   contextual parameters that are learned based on time series of the instantaneous parameters; processing the contextual parameters and the instantaneous parameters by utilizing a plurality of trained models by a plurality of estimators to determine a plurality of body temperature estimates, respectively;
   implementing bias and trend correction procedures to correct the plurality of body temperature estimates by improving trend matching and accuracy of the plurality of body temperature estimates;
   determining a confidence level of each of the plurality of body temperature estimates based on meta-features of a feature set that each of the plurality of estimators uses; and
   determining a final body temperature based on a combination of the plurality of body temperature estimates weighted based on the confidence level of each of the body temperature estimates.

9. The non-transitory computer-readable medium of claim 8, wherein the time series of the instantaneous parameters are determined by smoothing or filtering with different kernals including at least one of: low pass filtering, band pass filtering, high pass filtering, or wavelets to determine short-term dynamics of the instantaneous parameters.

10. The non-transitory computer-readable medium of claim 9, wherein as increased sensor data is accumulated, the smoothing is performed over longer time frames than the smoothing for the short-term dynamics to determine long-term dynamics of the instantaneous parameters.

11. The non-transitory computer-readable medium of claim 8, wherein the processing the contextual parameters and the instantaneous parameters is conducted through features extraction schemes.

12. The non-transitory computer-readable medium of claim 11, wherein the features extraction schemes include:
   processing the instantaneous parameters and the contextual parameters in overlapping or non-overlapping time windows to compute varying degree of moments including at least one of: mean, standard deviation, skew, or kurtosis, and
   measuring dispersion including at least one of: mean absolute difference, median absolute deviation, coefficient of variation, or entropy, to derive time domain features.

13. The non-transitory computer-readable medium of claim 11, wherein the features extraction schemes include:
   processing the instantaneous parameters and the contextual parameters in time windows to compute statistics of power density in at least one of different frequency sub-bands, cross spectrum, or coherence, to derive frequency domain features.

14. The non-transitory computer-readable medium of claim 11, wherein the features extraction schemes include:
   processing the instantaneous parameters and the contextual parameters in time windows to compute statistical information from short-term Fourier transform and wavelet transform to derive time-frequency domain features.

15. The non-transitory computer-readable medium of claim 11, wherein the features extraction schemes include processing the instantaneous parameters and the contextual parameters to derive information including time domain features, frequency domain features, and time-frequency domain features.

16. The non-transitory computer-readable medium of claim 15, wherein the derived information is appended into a universal set feature bank for further processing.

17. The non-transitory computer-readable medium of claim 16, wherein the plurality of body temperature estimates determined by the plurality of estimators is based on a subset of the universal set feature bank.

18. The non-transitory computer-readable medium of claim 17, wherein the plurality of body temperature estimates determined by the plurality of estimators is further based on prior training data that contains features of the universal set feature bank and a reference body temperature.

19. The non-transitory computer-readable medium of claim 18, wherein within each of the plurality of estimators, multiple versions are trained based on availability of features within the universal set feature bank, and a selector is employed to pick a high performing estimator.

20. A wearable sensor including a memory storing instructions to determine patient body temperature, and that, when executed, cause one or more processors to perform operations comprising:
measuring at least one of ambient, instantaneous, or patient condition sensor data of a patient; extracting from the at least one of ambient, instantaneous, or patient condition sensor data of the patient, two classes of parameters including:
instantaneous parameters that are entities that are derived based on the sensor data of the patient, and
contextual personalized parameters that are time series of the instantaneous parameters determined by smoothing or filtering with different kernels including at least one of: low pass filtering, band pass filtering, high pass filtering, or wavelets to determine short-term dynamics of the instantaneous parameters, and wherein as increased sensor data is accumulated, the smoothing is performed over longer time frames than the smoothing for the short-term dynamics to determine long-term dynamics of the instantaneous parameters;
processing the contextual personalized parameters and instantaneous parameters by utilizing a plurality of trained models by a plurality of estimators to determine a plurality of body temperature estimates, respectively;
implementing bias and trend correction procedures to correct the plurality of body temperature estimates by improving trend matching and accuracy of the plurality of body temperature estimates;
determining a confidence level of each of the plurality of body temperature estimates based on meta-features of a feature set that each of the plurality of estimators uses; and
determining a final body temperature based on a combination of the plurality of body temperature estimates weighted based on the confidence level of each of the body temperature estimates.

* * * * *